US00PP08685P

United States Patent [19]

Coward

[11] Patent Number: Plant 8,685

[45] Date of Patent: Apr. 12, 1994

[54] CHRYSANTHEMUM PLANT NAMED EARLY YELLOW VERO

[75] Inventor: Matthew G. Coward, Punta Gorda, Fla.

[73] Assignee: Burdette Coward & Company, Inc., Punta Gorda, Fla.

[21] Appl. No.: 19,890

[22] Filed: Feb. 19, 1993

[51] Int. Cl.[5] ..... A01H 5/00

[52] U.S. Cl. ..... Plt./82.2

[58] Field of Search ..... Plt. 82.1, 82.2

*Primary Examiner*—James R. Feyrer

*Attorney, Agent, or Firm*—Foley & Lardner

[57] ABSTRACT

A Chrysanthemum plant named Early Yellow Vero particularly characterized by its flat capitulum form; daisy capitulum type; yellow ray floret color; diameter across face of capitulum of up to 8 cm at maturity; flowering response of 8 to 8½ weeks under natural season flowering; medium plant height when grown as a single stem, and 15 to 20 cm peduncles on open, terminal sprays. Early Yellow Vero differs from the parent cultivar Early Vero only by its yellow flower color.

2 Drawing Sheets

The present invention comprises a new and distinct cultivar of Chrysanthemum, botanically known as *Dendranthema grandiflora,* and referred to by the cultivar name Early Yellow Vero.

The new cultivar is a mutation of the cultivar Early Vero, disclosed in my U.S. Plant Pat. No. 8,139. The new cultivar was discovered by the inventor on Jan. 5, 1991, growing among plants of the parent cultivar Early Vero in production beds of Burdette Coward & Co. Inc., Punta Gorda, Fla. The new cultivar was detected due to its yellow flower color. There was immediate interest in this new yellow mutation since it appeared to possess several characteristics that were superior to four other yellow daisy mutations that were being grown in test plots by the inventor. These are some of the characteristics of the new cultivar that were immediately apparent:

1. A darker yellow flower color than the other mutations being tested, its yellow flower color being identical to Yellow Vero, disclosed in U.S. Plant Pat. No. 6,943.

2. Earlier blooming than the other mutations tested, with its blooming period being identical to the parent Early Vero.

3. Ideal flower shape and form, being identical in appearance to the parent.

At the time of discovery, the cluster of yellow flowers that were produced by a single plant stood out by comparison to the thousand of white flowers of plants of Early Vero that surrounded it. The color was different, but all other traits were the same. The flowers were the same height, the foliage looked the same, the flowers were identical in shape and form to the parent plant, and the time to flowering was to the day exactly like Early Vero. Generally, Yellow Vero will not flower before November 15 when grown in Punta Gorda, Fla. under the conditions noted below. Under the same growing conditions, Early Yellow Vero flowers as early as November 1–2 based on natural growing conditions with no photoperiodic control. Thus, in early to mid-November, Early Yellow Vero provides an excellent cultivar to supply the normal market for Yellow Vero. This is a very important commercial advantage due in part to the seasonally high demand for yellow flowers that exists during early November. It has been verified that Early Yellow Vero blooms earlier than Yellow Vero at all times. Depending on the time of year and growing conditions, Early Yellow Vero blooms from 3 days to 10 days earlier than Yellow Vero.

In view of the potential importance of the earlier flowering characteristic of this new yellow daisy, the mutation was removed from the production bed and subsequently asexually propagated by the inventor on Mar. 12, 1991. Such propagation clearly established that the unique combination of characteristics as herein disclosed for Early Yellow Vero, including earlier flowering, are firmly fixed and are retained through successive generations of asexual reproduction. The complete stability of Early Yellow Vero has manifested itself in further generations of propagation up to the present time.

The primary difference between Early Yellow Vero and Yellow Vero is the flowering response and period. As mentioned, Early Yellow Vero flowers in early November. Flowering of Early Yellow Vero also extends into mid-May, and Early Yellow Vero blooms earlier than Yellow Vero at all times during the year. The only other differences noted to date are the slightly darker leaves of Early Yellow Vero and the tendency of Early Yellow Vero to be slightly shorter in overall height than Yellow Vero. The shorter plant height of Early Yellow Vero is probabily due to the fact that it buds faster and has several days less to grow. The difference in height is usually not more than approximately 3–4 inches. Apart from the noted differences, the characteristics of Early Yellow Vero and Yellow Vero appear to be identical. This is of particular significance since Yellow Vero is now recognized as perhaps the most outstanding yellow daisy cut spray mum on the market today.

It should be noted that the earlier flowering response of Early Yellow Vero has always expressed itself, but varies depending on the time of the year. For example, based on natural growing conditions in Punta Gorda, Fla. during late November, plants of Early Yellow Vero bloom approximately 6–7 days before plants of Yellow Vero. As the season progresses and the days length decreases in December and January, the difference in response periods between the respective cultivars tends to decrease. In those months Early Yellow Vero blooms approximately 3–4 days ahead of Yellow Vero. As the days again become longer moving toward spring, the relative difference in flowering response time again increases. From mid-April to early May, under natural flowering at production facilities in Punta Gorda, Early Yellow Vero again blooms approximately 6–7 days ahead of Yellow Vero. An important distinction is that by mid-May, Yellow Vero, which is more sensitive to day length, slows down and actually stops flowering while Early Yellow Vero continues to bloom. The term "sensitive" is used to signify reaction of the plant to longer days in natural growing conditions.

The earlier flowering response of Early Yellow Vero is of substantial economic advantage to growers. To those growers who are trying to maximize the natural season of Chrysanthemum production, it offers the option to extend the season both at the start and finish (early November and to and past mid-May). Thus, growers in Florida have the opportunity to reliably harvest Early Yellow Vero for Thanksgiving and Mothers Day. Yellow Vero will not flower dependably during those times, bearing in mind that shipments of cut flowers normally begin 10–14 days before each holiday.

For greenhouse growers the earlier flowering of Early Yellow Vero allows growers to recrop faster and accordingly make more efficient use of the areas devoted to pompon Chrysanthemum crops. In addition, Early Yellow Vero's earlier response is more compatible with other daisy and novelty Chrysanthemum varieties that are grown by commercial producers rather than or in addition to Yellow Vero. This allows more uniform cropping of the production areas and easier programming.

Test plots of the parent Early Vero were flowered in Costa Rica during October 1992. These tests established that Early Vero flowered 6 to 8 days faster than Vero and Yellow Vero in that particular environment as well. This is a considerable advantage for commercial growers in Costa Rica.

Early Yellow Vero has not been observed under all possible environmental conditions. The phenotype may very with variations in environment such as temperature, light intensity and daylength, without however, any variation in genotype. For example, trials to date have not included flowering of Early Yellow Vero beyond mid-May since it is normal to maximize production for the Mothers Day holiday. The quality of flowers significantly deteriorates at that time due to daylength and possibly temperature. It has been determined that Early Yellow Vero will flower uniformly in Florida until at least mid-May, and it may vary well flower well beyond that day under natural light conditions.

The following observations, measurements and comparisons describe plants of Early Yellow Vero grown in Punta Gorda, Fla. under natural season conditions which approximate those generally used in commercial practice. Natural season in Punta Gorda is between approximately November 1 through at least mid-May, and black cloth covering is not used. The plants are grown under saran cloth with 30% shade and no heat. During periods of decreased light in winter, lights are used to produce long days prior to the start of short days.

Tests have not been conducted on Early Yellow Vero under strict photoperiodic control regimens consisting of precise black cloth application. However, under short daylength natural growing conditions in mid-winter in Punta Gorda, it is expected that the difference between Yellow Vero and Early Yellow Vero in flowering response periods under a primarily photoperiodic regimen will be between 4–7 days.

The following traits have been repeatedly observed and are determined to be basic characteristic of Early Yellow Vero, which, in combination, distinguish this Chrysanthemum as a new and distinct cultivar:

1. Flat capitulum form.
2. Daisy capitulum type.
3. Yellow ray floret color.
4. Diameter across face of capitulum of approximately 8 cm at maturity.
5. The natural season flowering response ranges from 8–9 weeks, depending on the time of the year. For example, as above noted, short day treatment beginning September 1 will produce flowering on or about November 1. In mid-winter, the flowering response is a uniform 8 weeks.
6. Peduncle length ranges from 15 to 20 cm on open terminal sprays.
7. Medium plant height, requiring two long day weeks prior to short days to attain a flowered plant height of 100 to 110 cm for year-round flowerings. Early Yellow Vero is approximately 3–4 inches shorter than Yellow Vero when grown in Punta Gorda, Fla.
8. Its ability to uniformly flower in early November and in mid-May.

The accompanying color photographic drawings show the earlier flowering response of Early Yellow Vero, with plants of Early Yellow Vero being compared to plants of Yellow Vero and Early Vero. The photograph on Sheet 1 comprises flowering plants of Early Yellow Vero (on left) and Early Vero (on right) grown side by side. The photograph on Sheet 2 comprises plants of Yellow Vero (on left) and Early Yellow Vero (on right) grown under identical conditions. The plants shown in the photos were planted on Jan. 28, 1992, pinched on Feb. 10, 1992, subjected to short day treatment (lights out) on Mar. 5, 1992 and photographed on May 3, 1992. All of the plants shown were treated exactly the same during all stages of plant growth.

Referring to the photo on Sheet 1, the identical height, timing response and bloom shape of Early Yellow Vero and Early Vero is noted. Referring to the second photo which illustrates plants of Yellow Vero and Early Yellow Vero, Early Yellow Vero appears to be a somewhat lighter shade of yellow. The reason for this is that the blooms of Early Yellow Vero are completely opened and the buds of Yellow Vero are still in a tight stage. When flowers of the respective cultivars of the same maturity are compared, the flowers are identical in both color and appearance.

Of the commercial cultivars known to the inventor, the most similar in comparison to Early Yellow Vero, other than the parent Early Vero, is Yellow Vero. As above noted, Early Yellow Vero is identical to Yellow Vero except for its earlier flowering, somewhat shorter height, slightly darker foliage, and the ability to bloom during the longer daylength periods of May and November.

Early Yellow Vero can also be compared to the well known commercial yellow daisy Florida Marble. The response of Florida Marble is generally the same as Yellow Vero, although Florida Marble will bloom (non-uniformly) until mid-May and a few days earlier in November. Early Yellow Vero extends this daylength period of flowering, as noted. A further difference is that in early May flowerings, Florida Marble tends to exhibit foliage deterioration, increased bracting in the disc, and downward reflexing of the petals. In addition, Early Yellow Vero, similar to its parent Yellow Vero, is distinguished from Florida Marble by its much superior foliage, cleaner bloom, and somewhat smaller flower diameter.

In the following description color references are made to the Royal Horticultural Society Colour Chart.

Classification:

*Botanical.*—*Dendranthema grandiflora* cv Early Yellow Vero.

*Commercial.*—Daisy cut spray mum.

INFLORESCENCE

A. Capitulum:

*Form*—Flat.

*Type.*—Daisy.

*Diameter across face.*—Approximately 8 cm at maturity.

B. Corolla of ray florets:

*Color (general tonality from a distance of three meters).*—Yellow.

*Color (upper surface).*—5B when just opening; 4B when flower is completely open.

*Color (under surface).*—4C.

*Shape.*—Flat, oblong.

C. Corolla of disc florets:

*Color (nature).*—Closest to 12A to 12B.

*Color (immature).*—Closest to 144A to 144B.

D. Reproductive organs:

*Androecium.*—Present on disc florets only; scant pollen.

*Gynoecium.*—Present on both ray and disc florets.

PLANT

A. General appearance:

*Height.*—Medium; 100 to 110 cm as a flowering plant from a rooted cutting.

B. Folliage:

*Color (upper surface).*—147A.

*Color (under surface).*—147B.

*Shape.*—Lobed, slightly serrated.

I claim:

1. A new and distinct Chrysanthemum plant name Early Yellow Vero, as described and illustrated.

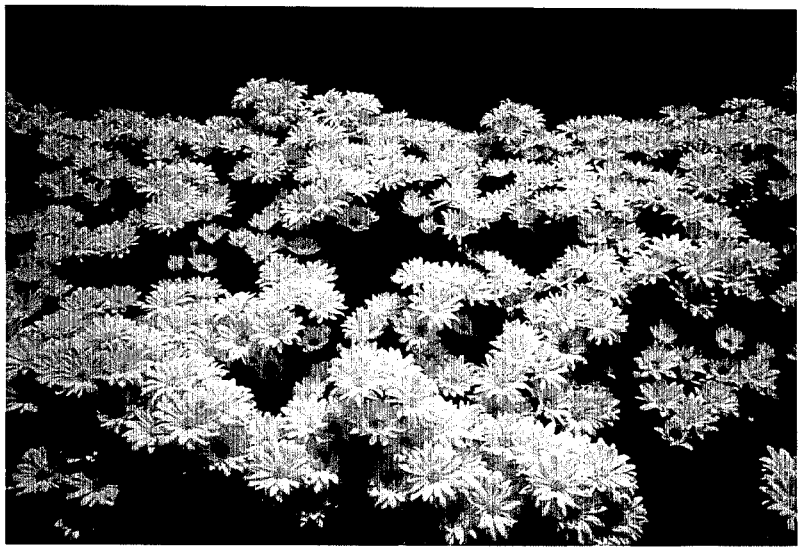

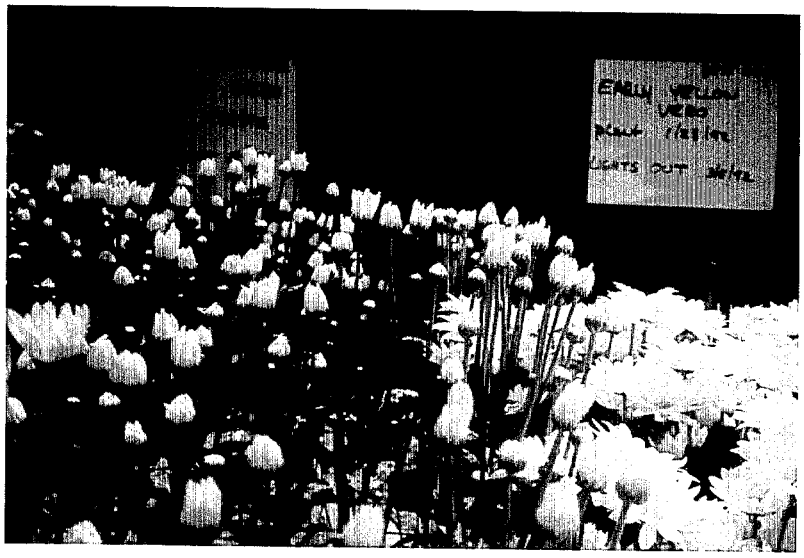

* * * * *